United States Patent
Koschnick et al.

(10) Patent No.: US 9,992,999 B2
(45) Date of Patent: Jun. 12, 2018

(54) SOLID AQUATIC HERBICIDE FORMULATIONS

(75) Inventors: Tyler J. Koschnick, Medina, OH (US); Hamid Ullah, Whitakers, NC (US)

(73) Assignee: SePRO Corporation, Carmel, IN (US)

( * ) Notice: Subject to any disclaimer, the term of this patent is extended or adjusted under 35 U.S.C. 154(b) by 542 days.

(21) Appl. No.: 12/416,649

(22) Filed: Apr. 1, 2009

(65) Prior Publication Data
US 2009/0247408 A1    Oct. 1, 2009

Related U.S. Application Data

(60) Provisional application No. 61/041,435, filed on Apr. 1, 2008.

(51) Int. Cl.
| | |
|---|---|
| *A01N 43/40* | (2006.01) |
| *A01N 39/04* | (2006.01) |
| *A01N 25/08* | (2006.01) |
| *A01N 25/12* | (2006.01) |

(52) U.S. Cl.
CPC .............. *A01N 43/40* (2013.01); *A01N 25/08* (2013.01); *A01N 25/12* (2013.01); *A01N 39/04* (2013.01)

(58) Field of Classification Search
CPC ........ A01N 43/40; A01N 39/04; A01N 25/12; A01N 25/08
USPC ....................................................... 504/254
See application file for complete search history.

(56) References Cited

U.S. PATENT DOCUMENTS

| | | |
|---|---|---|
| 5,466,693 A | 11/1995 | Warrington et al. |
| 5,843,203 A | 12/1998 | Lindsay et al. |
| 5,883,047 A | 3/1999 | Jaeger et al. |
| 6,337,078 B1 | 1/2002 | Levy |
| 6,825,151 B2 | 11/2004 | Harwell |
| 6,890,888 B2 | 5/2005 | Pursell et al. |

OTHER PUBLICATIONS

Renovate OTF Aquatic Herbicide Material Safety Data Sheet, 2006, SePRO, pp. 1-4.*
Fresenburg, B., Home Lawn Weed Control, MU Guide, 2005, MU Extension, University of Missouri—Columbia, pp. 1-4.*
Turflon II Amine Material Safety Data Sheet, 1997, Riverdale, pp. 1-4.*
"1.2 1992 Environmental Impact Statement and Effects of State Senate Bill 5424," Herbicide Risk Assessment for the Aquatic Plant Management Final Supplemental Environmental Impact Statement, Appendix C, vol. 3: 2,4-3, Feb. 2001, 2 pages.
Material Safety Data Sheet AB Navigate, Advantis Technologies, Inc., Manufacturer, Feb. 15, 2007, 4 pages.
www.kadantgrantek.com/biodac/commercial, Commercially Available Formulations of Biodac, last printed Feb. 20, 2008, 1 page.
www.kadantgrantek.com/biodac/composition, Composition and Properties of Biodac, last printed Feb. 27, 2008, 2 pages.

* cited by examiner

*Primary Examiner* — John Pak
*Assistant Examiner* — Andriae M Holt
(74) *Attorney, Agent, or Firm* — Woodard, Emhardt, Moriarty, McNett & Henry, LLP

(57) ABSTRACT

Described are preferred formulations comprising amine salts of 2,4-D or triclopyr or both, loaded on a granular carrier including plant fiber and mineral filler, 5 and optionally a binder. Also described are methods of making and using such compositions.

15 Claims, No Drawings

SOLID AQUATIC HERBICIDE FORMULATIONS

REFERENCE TO RELATED APPLICATIONS

The present application claims the benefit of U.S. Provisional Patent Application No. 61/041,435, filed Apr. 1, 2008, entitled SOLID AQUATIC HERBICIDE FORMULATIONS, which is hereby incorporated herein by reference in its entirety.

BACKGROUND

The present invention relates generally to the control of aquatic weeds, and in particular to granulated aquatic herbicide compositions and their use in the control of aquatic weeds.

As further background, various methods exist for the control of aquatic weeds. The selection of an appropriate control method depends upon many factors such as environmental impact, cost effectiveness, efficacy, and the like. The various control methods available include physical controls such as mechanical harvesting, hand pulling or cutting, or the use of bottom barriers or water level drawdown. These methods can be both time consuming and labor intensive, and can create significant environmental disturbance, especially when considered on a large scale.

Biological controls such as the use of triploid grass carp can be desirable in some aquatic systems in that they reduce the use of equipment and have the potential for long term control of aquatic weeds. Nonetheless, in many aquatic systems, triploid grass carp often completely remove all aquatic vegetation for many years. The long-term environmental impacts result in reluctance of many natural resource managers to use triploid grass carp for these purposes. In temperate aquatic systems, the efficacy of such biological controls can also vary widely, and is dependent upon factors such as feeding preferences, metabolism, temperature, and stocking rate.

For these and other related reasons, the use of aquatic herbicides has become a common method for controlling invasive aquatic weeds. The use of herbicidal control nonetheless also presents risks and difficulties including the potential impact on the local environment, maintaining duration of herbicide exposure to control weeds in flowing water, selectivity to non-target species, the potential for excessive decrease in the dissolved oxygen (DO) content of the waters due to rapid plant decay, and possible toxicity to other life-forms.

In view of the background in this area, there are needs for improved and/or alternative aquatic herbicide formulations, and methods for their preparation and use. The present invention is addressed to these needs.

SUMMARY

In one aspect, the present invention relates to granular aquatic herbicidal compositions that effectively and stably entrain or incorporate one or more aquatic herbicides. In particular embodiments, granular aquatic herbicidal compositions of the invention employ a carrier that contains a complex of a material including plant fiber, such as paper or wood, a mineral filler material such as one or more clays or carbonates and optionally a binder, such as starch. Such a carrier stably incorporates aquatic herbicides that are provided as a typically water soluble amine salt at surprising, high levels, while avoiding significant exterior caking or dusting of the formulation.

In one embodiment, the present invention provides a granular aquatic herbicide for controlling aquatic weeds. The granular aquatic herbicide comprises a granular carrier including a complex of plant fiber (e.g. paper fiber or cellulose) and clay and/or another inorganic material, and may include a binder, typically an organic material such as starch. One or more water soluble or dispersible amine salt-form herbicidal agents are incorporated into the carrier, and in particular embodiments one or both of an amine salt of 2,4-dichlorophenoxyacetic acid (2,4-d) or an amine salt of [(3,5,6-Trichloro-2-pyridinyl)oxy]acetic acid (triclopyr). Free acid forms of these two or other herbicidal agents (alone or combined) may also be used on the plant fiber/clay granular carriers as identified herein in additional aspects of the invention. In preferred forms, the density of the carrier plus the herbicidal agent is greater than that of water so that the granules will sink when applied to an aquatic environment. In certain forms, the granular aquatic herbicide composition can comprise from about 1% to about 35% of an amine salt of triclopyr by weight incorporated into the granular carrier, more preferably about 20% to about 35% by weight. In certain forms, the aquatic herbicide composition comprises from about 1% to about 35% of an amine salt of 2,4-d by weight incorporated into the granular carrier, more preferably about 20% to about 35% by weight. In other forms, the granular composition comprises from about 5% to about 25% by weight of an amine salt of triclopyr amine and from about 10% to about 30% by weight of an amine salt of 2,4-d incorporated in combination in the granular carrier.

Another aspect of the invention is the method for controlling aquatic weeds comprising applying to an aquatic environment including the weeds an effective amount of a granular herbicide product, where the granular herbicide product comprises a granular carrier containing a complex of paper fiber, mineral filler and optionally an organic binder and incorporating into the granular carrier an herbicide for controlling aquatic weeds. The preferred herbicides to be incorporated into the granular carrier are amine salts of 2,4-d or triclopyr, singularly or in combination each other.

Still additional aspects of the invention relate to methods for preparing granular herbicidal compositions that involve incorporating one or more amine salt herbicides into a granular carrier comprising plant fiber and mineral filler.

Additional embodiments as well as features and advantages of the invention will be apparent to those of ordinary skill in the art from the descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

In certain preferred embodiments, the present disclosure provides herbicidal formulations loaded on a granule or other carrier useful for the control of aquatic plants, wherein the formulations include 2,4-d or triclopyr or both loaded upon a solid support comprising a complex of a cellulosic material such as paper fiber, and clay. The present disclosure also provides methods for controlling aquatic plants which comprise introducing into a body of water having the plants an effective amount of an aquatic herbicide formulation of the invention.

The chemical 2,4-d is formally known as 2,4-dichlorophenoxyacetic acid and is an herbicide in the phenoxyacetic acid family. Triclopyr is formally known as 3,5,6-trichloro-2-pyridyloxyacetic acid and is an herbicide in the picolinic acid family. Both 2,4-d and triclopyr herbicides are systemic agents used post-emergence for selective control of broadleaf weeds (dicots) and neither are effective against most grasses (monocots). The modes of action of 2,4-d and triclopyr are as plant hormone mimics (auxin). These types of herbicides kill the target weed by mimicking the plant growth hormone auxin (indole acetic acid), and when administered at effective doses, causes uncontrolled and disorganized plant growth that leads to plant death. 2,4-d dimethylamine salt formulation is a preferred product used in embodiments of the present disclosure, and is sold under the trade name DMA-4® or DMA-6® from Dow AgroSciences, Indianapolis, Ind., USA. 2,4-d dimethylamine salt is also a preferred form for aquatic use because it is substantially less toxic to other creatures, such as fish, than the butoxyethyl ester of 2,4-d. 2,4-d amine is more soluble in water than the water dispersible butoxyethyl ester form providing an increased mobility of the amine form in water and increasing the effectiveness of the treatment.

In an aquatic environment, 2,4-d products have good effectiveness against various plant species including various milfoil species (*Myriophyllum* spp.) and water stargrass (*Heteranthera dubia*). At higher rates of applications, 2,4-d products are also effective against bladderwort (*Utricularia* spp.), white waterlily (*Nymphaea* spp.), spatterdock or yellow water lily (*Nuphar* spp.), water shield (*Brasenia* spp.), water chestnut (*Trapanatans*), coontail (*Ceratophyllum demersum*) and Marine eelgrass (*Zostera marina*). Spatterdock and coontail are often difficult to control and multiple treatments, separated by a period of time specified in the label or permit, may be necessary to achieve full control.

Some triclopyr products are registered for use in aquatic environments for control of emersed, submersed and floating aquatic plants in environments such as ponds, lakes, reservoirs, non-irrigation canals, seasonal irrigation waters and ditches which have little or no continuous outflow, marshes, and wetlands, including broadleaf and woody vegetation on banks and shores within or adjacent to these and other aquatic sites. Current commercial triclopyr products exist as the soluble triethylamine salt or the water dispersible butoxyethyl ester. Triclopyr triethylamine salt is the preferred form used in a number of embodiments of the present invention, and is sold under the trade name RENOVATE 3® from SePRO Corporation, Carmel, Ind. Triclopyr triethylamine is preferred for aquatic use because it is substantially less toxic to creatures such as fish, than the butoxyethyl ester of triclopyr. Triclopyr amine is more soluble in water than the butoxyethyl ester form providing an increased mobility of the amine form in water and increasing the effectiveness of the treatment.

In an aquatic environment, triclopyr products are effective against such things as various milfoil species (*Myriophyllum* spp.), alligatorweed (*Alternanthera philoxeroides*), white waterlily (*Nymphaea* spp), spatterdock or yellow water lily (*Nuphar* spp.), water shield (*Brasenia* spp), american lotus (*Nelumbo lutea*), american frogbit (*Limnobium spongia*), aquatic soda apple (*Solanum tampicense*), pickerelweed (*Pontederia* spp.), purple loosestrife (*Lythrum salicaria*), water hyacinth (*Eichhornia crassipes*), water primrose (*Ludwigia* spp.), pennywort (*Hydrocotyle* spp.), parrotfeather (*Myriophyllum aquaticum*) and a variety of other plant species. Parrotfeather is often difficult to control and multiple treatments, separated by a period of time specified in the label or permit, may be necessary to achieve full control.

The present invention provides in one aspect a solid herbicidal composition comprising an amine salt of either 2,4-d or triclopyr, or both, and a granulated clay and plant fiber (e.g. paper) carrier. A preferred granulated carrier is commercially available under the tradename BIODAC® from Kadant GranTek Inc. of Green Bay, Wis., USA. BIODAC® granular carrier is an agglomerated carrier comprised of paper and clay. It is resistant to attrition, leaving its particle size distribution unaffected by transportation and application. BIODAC® granular carrier degrades into elements naturally occurring in the soil, and the carrier is made from recycled paper products or the waste generated by paper mills. BIODAC® granular carrier is available in standard particles sizes of 4/10 mesh, 10/30 mesh, 12/20 mesh, and 20/50 mesh (U.S Sieve Series). Another preferred carrier is commercially available under the tradename ECO GRANULE QD™ and ECO GRANULE HW™ from Cycle Group, Inc. of Mocksville, N.C., USA. ECO GRANULE QD™ or ECO GRANULE HW™ carrier is comprised of hardwood fibers, calcium carbonate and an organic binder, and is available in a 12/40 mesh particle size. For a tabulation of U.S. Sieve Series screen nomenclature, see Perry's Chemical Engineering Handbook, 7th Ed., McGraw-Hill, Inc., New York, N.Y. (1997), p. 19-20 (Table 19-6). The first number of the pair indicating the particle size is the mesh size where at least 95% of the granular particles pass through the mesh and the second number is the mesh size where no more than 5% of the granular particles pass through the mesh.

Methods of preparing agglomerated carriers including plant fiber such as cellulose and clay are disclosed, for example, in U.S. Pat. No. 4,560,527. A granulated carrier may also comprise cellulose fibers and mineral filler, and optionally an organic binder wherein each particle or granule of the carrier comprises a mixture of cellulose fibers and mineral filler, and optionally an organic or other binder material. In certain aspects of the invention, the granular carrier is comprised of 10-90% of a plant fiber material and 10-90% of a mineral filler such as one or more clays or carbonates, and optionally about 1-10% organic binder, such as starch. More preferably, the carrier is comprised of about 20-50% plant fiber (especially cellulosic material) and about 80-50% of the mineral filler, and optionally about 1-10% binder. In another aspect, the carrier is comprised of about 30-50% plant fiber (especially cellulosic material) and about 70-50% of the mineral filler, and optionally about 1-10% binder. In other preferred aspects, the plant fiber/mineral carrier granules contain at least 30% by weight of cellulosic fibers.

In certain embodiments, the carrier granules of the herbicidal material have a density greater than water. In this manner, the granules have the capacity to sink when applied to an aquatic environment and will thus substantially avoid wind-driven or surface current-driven drift from the point of their application to a water body. As well, it is preferred that the granules have a density, shape and size such that they will break the surface tension of water when surface-applied to the water body, and thereafter sink.

In preferred forms, the herbicide-loaded carrier granules will be free from any coating that retards release of the herbicide(s) from the carrier. With no coating retarding release of the herbicides in such formulations, the herbicide freely diffuses out of the granules so as to more quickly provide a minimum target concentration of the herbicide in the water body under treatment.

In certain embodiments, the granular aquatic herbicide composition of the invention comprises from about 1% by weight to about 35% by weight of an amine salt of triclopyr, more preferably about 20% to about 35% by weight. In this regard, unless otherwise indicated, all weight percents given herein are on a weight:weight basis. In other embodiments, the granular aquatic herbicide composition of the invention comprises from about 1% to about 35% by weight of an amine salt of 2,4-d, more preferably from about 20% to about 35% by weight. In still further embodiments, the granular aquatic herbicide of the invention comprises from about 5% to about 25% by weight of an amine salt of triclopyr and from about 10% to about 30% by weight of an amine salt of 2,4-d. Granular formulations that are relatively highly loaded with the 2,4-d, triclopyr, and/or other amine salt herbicidal agent will be preferred, including those formulations loaded with at least 10% by weight of the herbicidal agent(s), alone or combined. The remainder of the weight of the compositions of the above formulations can be constituted essentially from the carrier material, e.g. with the remainder constituted 90% to 100% by the carrier material. Additional materials that can be included in the composition include for example adjuvants such as surfactants, antifoam agents, and the like. Other active agents, such as additional herbicides, may also be included.

When incorporating a combination of herbicidal agents into the granular carrier, the agents can be applied in separate liquid formulations or admixed in a single liquid formulation. When applied in separate liquid formulations, an intermediate drying step can optionally be performed in between applications, or can be omitted. Additionally, the separate liquid formulations can be applied simultaneously or sequentially, or any combination thereof. These and other variations for achieving the combined incorporation of the agents in the carrier will be apparent those skilled in the field from the descriptions herein.

In use, the granular formulations of the invention will be applied to the body of water in sufficient amount to release and establish an effective level of the herbicide to control the target weed or weeds. Typically, when using a granular composition incorporating a triclopyr herbicide as the sole herbicidally active agent, levels of triclopyr of about 0.05 ppm to about 2.5 ppm will be established in the treated water body. When using a granular composition incorporating a 2,4-d herbicide as the sole herbicidally active agent, levels of 2,4-d of about 0.1 ppm to about 4 ppm will be established in the treated water body. When using a granular composition incorporating both a triclopyr herbicide and a 2,4-d herbicide, levels of about 0.04 to 2.0 ppm and about 0.08 to 3.2 ppm, respectively, will be established in the water body.

In additional embodiments, other dissociable derivatives of 2,4-d, triclopyr, or other similar herbicidal agents can be used in addition to or in place of the amine salt forms disclosed herein, in similar amounts and ratios to those disclosed herein. In particular embodiments, the free acid forms of 2,4-d, triclopyr, or other herbicides are used alone or in combination on the plant fiber/mineral carriers as described herein.

For the purpose of promoting a further understanding of embodiments of the invention as well as features and advantages thereof, the following specific Examples are provided. It will be understood that these Examples are illustrative, and not limiting, of the invention.

EXAMPLES 1-7 (COMPARATIVE)

Numerous attempts were made to prepare granular formulations of triclopyr amine on carriers commonly used in granular herbicide formulations, as outlined in Table 1. In particular, an appropriate amount of a liquid herbicide solution of triclopyr amine (RENOVATE 3®) was combined and mixed with the appropriate amount of the specified solid carrier, followed if required by air drying, in an attempt to make the herbicidal formulation. In all cases reported in Table 1, the common carriers failed to sufficiently absorb the herbicide material, and upon drying, a crystalline material formed on the outside of the granules which caused problems with dusting.

TABLE 1

| Example | RENOVATE 3A® (% wt./wt.) | Solid Support (% wt./wt.) | Results |
| --- | --- | --- | --- |
| 1 | 31.6 | Fuller's Earth Granules, Oil Dri Corp. 68.4 | Failure, lack of absorption, dust issues |
| 2 | 32.0 | TERRA GREEN FAST PLAY®, Oil Dri Corp. 68.0 | Failure, lack of absorption, dust issues |
| 3 | 31.6 | RVM clay, Oil Dri Corp. 68.4 | Failure, lack of absorption, dust issues |
| 4 | 31.6 | ATTASORB LVM®, BASF Corp. 68.4 | Failure, lack of absorption, dust issues |
| 5 | 31.6 | montmorillonite 68.4 | Failure, lack of absorption, dust issues |
| 6 | 31.6 | LVM clay Oil Dri Corp. 68.4 | Failure, lack of absorption, dust issues |
| 7 | 32.0 | ECOGRANULE AX® Cycle Group Inc. 68.0 | Failure due to lack of liquid holding capacity |

EXAMPLES 8-10 (INVENTIVE)

The procedure of Examples 1-7 was repeated, except substituting a BIODAC® paper/clay agglomerate carrier as outlined in Table 2. The formulations produced were stable, free flowing, mostly dust-free dry material. The exterior surfaces of the granules were substantially free from the crystalline material layer observed in Examples 1-7.

TABLE 2

| Example | RENOVATE 3A® (% wt./wt.) | Solid Support (% wt./wt.) | Results |
| --- | --- | --- | --- |
| 8 | 32.0 | BIODAC 12/20® Kadant GranTek Inc. 68.0 | Successful |
| 9 | 32.0 | BIODAC 10/30® Kadant GranTek Inc. 68.0 | Successful |
| 10 | 32.0 | BIODAC 4/10® Kadant GranTek Inc. 68.0 | Successful |

EXAMPLES 11-19 (INVENTIVE)

The procedure of Examples 1-7 was repeated, except substituting a BIODAC® paper/clay agglomerate carrier combined with triclopyr amine and/or 2,4-d amine as outlined in Table 3. The formulations produced were stable, free flowing, mostly dust-free dry material. The exterior surfaces of the granules were substantially free from the crystalline material layer observed in Examples 1-7. Non-replicated storage stability was evaluated at 54° C. for 2 to 3 weeks with each a formulation of 2,4-d (DMA 6: 32% by weight) or triclopyr (Renovate 3: 32% by weight) with acceptable results.

TABLE 3

| Component | Example (% wt./wt.) | | | | | | | | |
|---|---|---|---|---|---|---|---|---|---|
| | 11 | 12 | 13 | 14 | 15 | 16 | 17 | 18 | 19 |
| RENOVATE 3A ® | 0 | 0 | 15.85 | 6.30 | 9.50 | 12.70 | 9.04 | 12.55 | 0 |
| DMA-4 ® | 26.00 | 32.00 | 15.85 | 25.40 | 22.20 | 19.10 | 0 | 0 | 0 |
| DMA-6 ® | 0 | 0 | 0 | 0 | 0 | 0 | 20.96 | 19.45 | 32.00 |
| BIODAC ® | 74.00 | 68.00 | 68.30 | 68.30 | 68.30 | 68.20 | 70.00 | 67.5 | 68.00 |
| Amount of acid equivalence in formulation (% a.e.) | | | | | | | | | |
| Triclopyramine salt | 0 | 0 | 5.04 | 2.00 | 3.02 | 4.04 | 2.87 | 3.99 | 0 |
| 2,4-d amine salt | 9.98 | 12.29 | 6.09 | 9.75 | 8.52 | 7.33 | 11.63 | 10.79 | 17.76 |

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A granular aquatic herbicide composition, comprising:
   a granular carrier comprising agglomerated granules including plant fiber and mineral filler, said agglomerated granules having a density greater than water, wherein the granules are comprised about 20 to 50% of the plant fiber and about 80 to 50% of the mineral filler; and
   an amine salt of triclopyr or an amine salt of 2,4-D incorporated in the granular carrier, wherein the amine salt of triclopyr or the amine salt of 2,4-D is present in an amount of at least 10% by weight of the composition; and
   wherein the composition is substantially free of any crystalline layer of the amine salt of triclopyr or the amine salt of 2,4-D on the outer surface of said granules; and
   wherein the granules are free from any coating that retards release of the amine salt of triclopyr or the amine salt of 2,4-D from the granules.

2. The herbicide composition of claim 1, wherein the plant fiber comprises a cellulosic fiber material.

3. The herbicide composition of claim 2, wherein the cellulosic fiber material is paper or hardwood fiber.

4. The herbicide composition of claim 1, wherein the mineral filler is clay or calcium carbonate.

5. The herbicide composition of claim 1, wherein the granular carrier further comprises an organic binder.

6. The herbicide composition of claim 1, wherein an amine salt of triclopyr is incorporated in the granular carrier.

7. The herbicide composition of claim 6, wherein the amine salt of triclopyr is a triethylamine salt of triclopyr.

8. The herbicide composition of claim 1, wherein an amine salt of 2,4-D is incorporated in the granular carrier.

9. The herbicide composition of claim 8, wherein the amine salt of 2,4-D is a dimethylamine salt of 2,4-D.

10. The herbicide composition of claim 1, wherein a mixture of herbicides including an amine salt of triclopyr and an amine salt of 2,4-D is incorporated in the granular carrier.

11. The herbicide composition of claim 10, wherein the amine salt of triclopyr is a triethylamine salt of triclopyr, and the amine salt of 2,4-D is a dimethylamine salt of 2,4-D.

12. The herbicide composition of claim 11, wherein the triclopyr triethylamine salt is present in an amount from 10% to about 25% by weight and the 2,4-D dimethylamine is present in an amount from 10% to about 30% by weight.

13. A method for controlling aquatic weeds, comprising:
   applying to an aquatic environment including the weeds an effective amount of a granular herbicide product according to claim 1.

14. The method of claim 13, wherein the aquatic environment is a freshwater body.

15. The method of claim 14, wherein the aquatic weeds include a milfoil species.

* * * * *